US00PP35515P3

(12) United States Plant Patent
Olesen

(10) Patent No.: US PP35,515 P3
(45) Date of Patent: Dec. 5, 2023

(54) ROSE PLANT NAMED 'POULREN036'

(50) Latin Name: *Rosa hybrida*
Varietal Denomination: Poulren036

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 58 days.

(21) Appl. No.: 17/803,630

(22) Filed: Sep. 13, 2022

(65) Prior Publication Data

US 2023/0140855 P1 May 4, 2023

(30) Foreign Application Priority Data

Sep. 24, 2021 (QZ) ..... PBR 2021/2357

(51) Int. Cl.
*A01H 5/02* (2018.01)
*A01H 6/74* (2018.01)

(52) U.S. Cl.
USPC ..... Plt./130
CPC ..... *A01H 6/749* (2018.05)

(58) Field of Classification Search
USPC ..... Plt./130
CPC ..... A01H 6/749; A01H 5/02
See application file for complete search history.

(56) References Cited

PUBLICATIONS

Poulsen Roser A/S (Year: 2023).*

* cited by examiner

*Primary Examiner* — Keith O. Robinson

(57) ABSTRACT

A new garden rose plant of the Hybrid Tea class which has abundant, pink orange blend flowers and attractive foliage. This new and distinct variety has shown to be uniform and stable in the resulting generations from asexual propagation.

2 Drawing Sheets

Botanical designation: *Rosa hybrida.*

Variety denomination: 'Poulren036'.

This application claims priority to Plant Breeder's Rights Application Number 2021/2357, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulren036', originated as a single seedling from the stated cross.

The new variety may be distinguished from its male pollen parent and female seed parent primarily by the following characteristics. The male pollen parent plant has yellow flowers while the new variety has pink orange blend flowers. The female seed parent plant has salmon pink flowers while the new variety has pink orange blend flowers.

The objective of the hybridization of this rose variety was to create a new and distinct variety with unique qualities, such as:

1. Uniform and abundant pink orange blend flowers;
2. Vigorous, but compact growth when propagated on its own roots;

3. Exceptional disease resistance; and
4. Strong perfume.

This combination of qualities is not present in previously available commercial cultivars of this type, known to the inventor, and distinguish 'Poulren036' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulren036' was selected in the spring of 2013 by the inventor as a single plant from the progeny of the aforementioned hybridization.

Asexual reproduction of 'Poulren036' by rooted cuttings was first done by Mogens N. Olesen in the nursery in Fredensborg, Denmark in July, 2013. This initial and other subsequent asexual propagations conducted in controlled environments have demonstrated that the characteristics of 'Poulren036' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren036'.

Specifically illustrated in FIG. 1 of the drawings are open flower viewed from above, a cluster of open flowers on a branch, flower petals detached, reproductive flower parts, a flower bud upon opening, and sepals detached.

Figure 1:
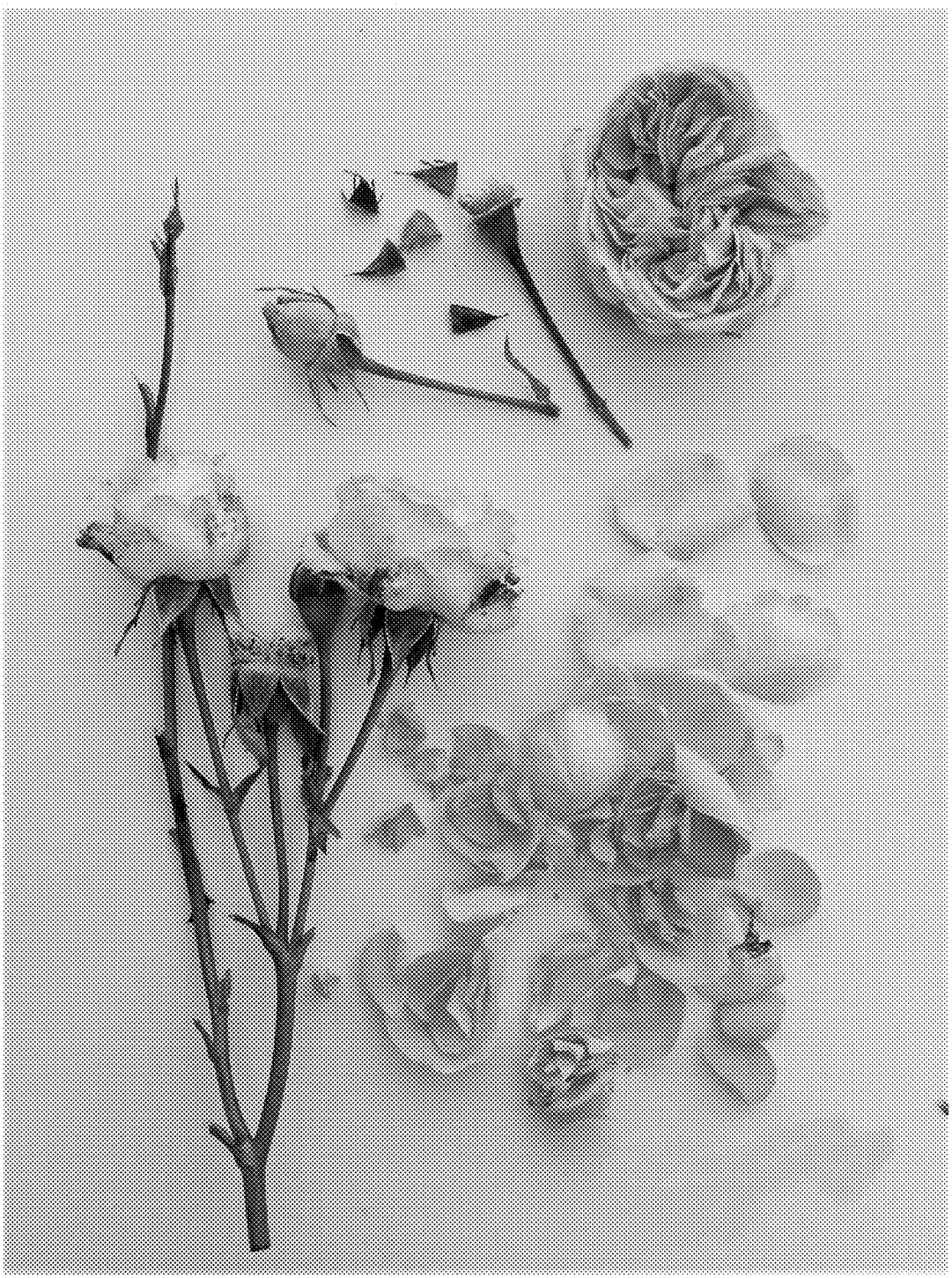
Figure 2:
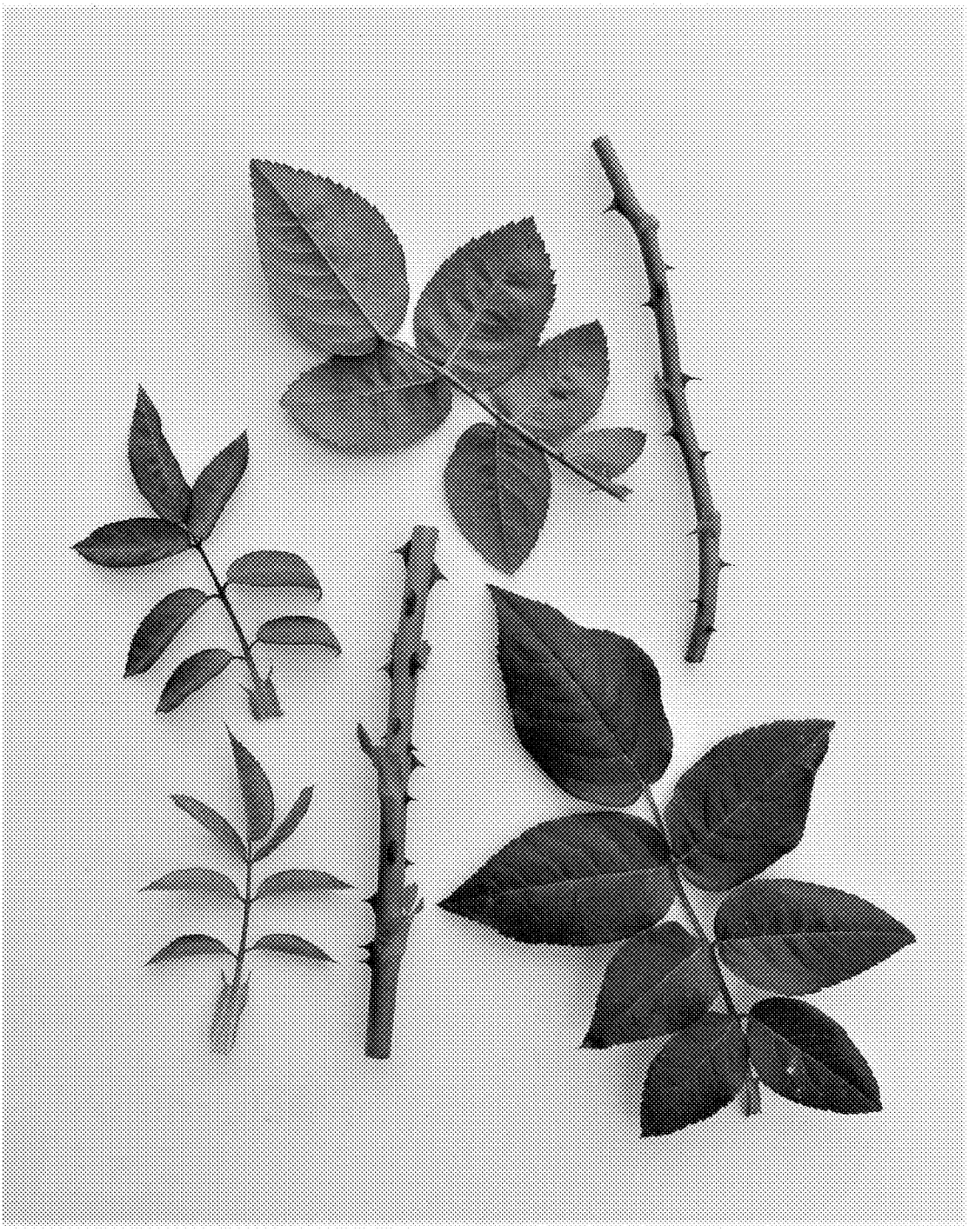

Specifically illustrated in FIG. 2 of the drawings are juvenile and mature leaves, and bare stems exhibiting prickles. Plants shown are 2 years of age.

DETAILED DESCRIPTION OF THE VARIETY

The following is a description of 'Poulren036', as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulen009', U.S. Plant Pat. No. 15,887 are now compared to 'Poulren036'. While the comparison variety has a petal count of 45 petals, the claimed plant has 107 flower petals. The general tonality of open flowers for the comparison variety is Red Group 54D with intonations of Red Group 52C. The general tonality of open flowers for the claimed plant is Red Group 38C with other intonations of Orange Group 24C.

FLOWER AND FLOWER BUD

Blooming habit: Continuous.

Flower bud:

- *Size.*—Upon opening, 27 mm in length from base of receptacle to end of bud. Bud diameter is 17 mm.
- *Bud form.*—Ovoid.
- *Bud color.*—As sepals divide petals are Yellow Group 11B with splashes of Red Group 53B.
- *Sepal inner surface.*—Color: Yellow-Green Group 146D. Surface: Lightly pubescent.
- *Sepal outer surface.*—Color: Yellow-Green Group 144A with intonations of Greyed-Purple Group 183B. Texture: Smooth.
- *Sepal shape.*—Apex: Cirrhose. Base: Flat at union with receptacle.
- *Sepal margin.*—Margins have moderate foliaceous appendages on three of the five sepals.
- *Sepal size.*—About 31 mm long, 12 mm wide.
- *Receptacle.*—Texture: Smooth. Size: 12 mm in height, 11 mm wide. Color: Yellow-Green Group 144A with intonations of Greyed-Red Group 181B. Shape: Campanulate.
- *Pedicel.*—Surface: Smooth. Length: 60 mm. Diameter: 3 mm on average. Color: Yellow-Green Group 144B. Strength: Strong.
- *Peduncle.*—Length: 3 to 5 cm. Diameter: About 3 mm. Color: Yellow-Green Group 144A. Texture: Smooth.

Flower bud development: Flower buds are borne in clusters of 3 flower buds per stem, on average. Development as a panicle.

Flower bloom:

- *Fragrance.*—Strong perfume.
- *Duration.*—The blooms have a duration on the plant of approximately 14 days. Petals fall cleanly away from plant after flowers have fully matured.
- *Size.*—Flower diameter is 85 mm when open. Flower depth is 40 mm.
- *Flower shape.*—Quartered-rosette, very double, with many overlapping petals packed into quarter sections.
- *Shape of flower, side view.*—The upper portion is flat. The lower portion is flat concave.

Petalage: Under normal conditions, flowers have about 107 petals.

General tonality of flower: Open flowers are Red Group 38C with other intonations of Orange Group 24C.

Petal color:

- *Upon opening, outer petals.*—Upper surface: Red Group 56A. Lower surface: Red Group 56D.
- *Upon opening, inner petals.*—Upper surface: Orange-Red Group 32C with a basal zone color Yellow-Orange Group 14B. Lower surface: Orange Group 24C blended with Yellow Group 11B.
- *Basal petal spots, upon opening.*—Upper surface: Large Yellow Group 11A. Lower surface: Large Yellow Group 10A.
- *After opening.*—The outer and inner petals have the same colour as found in the petals upon opening.

Petals:

- *Petal reflex.*—Somewhat reflexed.
- *Margin.*—Single or multiple deep cleft at margin. Moderate undulations.
- *Shape.*—Broad and elliptic. Apex shape: Rounded. Base shape: Acute.
- *Size.*—40 mm (l)×43 mm (w).
- *Texture.*—Smooth on the upper and lower surfaces.
- *Thickness.*—Average.

Petaloids:

- *Size.*—26 mm (l) by 20 mm (w).
- *Quantity.*—About 24.
- *Shape.*—Elliptical with an acute base and rounded apex.
- *Color.*—The upper surface is Orange-Red Group 32C with a basal zone color Yellow-Orange Group 14B. At the point of attachment Yellow 10A. The lower surface is Orange Group 24C blended with Yellow Group 11B. Yellow 10A at basal zone.

Reproductive flower parts:

- *Pollen.*—None observed.
- *Anthers.*—Size: 2 mm in length. Color: Yellow-Orange Group 16A. Quantity: 40 on average.
- *Filaments.*—Color: Yellow Group 12A. Length: 6 mm.
- *Pistils.*—Length: 4 mm. Quantity: 36 on average.
- *Stigmas.*—Color: Yellow-White Group 158A.
- *Styles.*—Color: Green-White Group 157A with intonations of Red-Purple Group 58C.
- *Location of stigmas.*—Inferior in location relative to the length of the filaments and the height of the anthers.
- *Hips.*—None Observed.

PLANT

Plant growth: Upright. Plants are 51 cm in height, and 55 cm wide.

Stems:

- *Color of juvenile growth.*—Yellow-Green Group 144A with intonations of Greyed-Purple Group 183B.
- *Color of mature growth.*—Yellow-Green Group 144A.
- *Length.*—Canes are about 30 cm from the base of the plant to the flowering portion.
- *Diameter.*—About 6 to 8 mm.
- *Internodes.*—On mature canes about 45 mm between nodes.
- *Surface texture.*—Young wood: Smooth. Older wood: Smooth.

Long prickles:

*Incidence*.—About 14 prickles per 10 cm of stem.

*Size*.—Average length of prickles on mature stems is 7 mm.

*Shape*.—Upper portion is linear. Lower portion is concave.

*Color*.—Juvenile prickles: Greyed-Purple Group 183B. Mature prickles: Greyed-Purple Group 183B.

Plant foliage:

*Compound leaf*.—200 mm (l)×145 (w).

*Quantity*.—2 leaves per 10 cm of stem on average.

*Leaf bearing angle to the stem*.—45 degrees.

*Color of juvenile foliage*.—Upper side: Yellow-Green Group 144A with intonations of Greyed-Red Group 178B at the margins. Lower side: Yellow-Green Group 144B shaded with Greyed-Red Group 178B.

*Color of mature foliage*.—Upper side: Yellow-Green Group 147A. Lower side: Yellow-Green Group 146B.

Plant leaves and leaflets:

*Stipules*.—Size: 18 mm long, 3 mm wide. Quantity: 2 per compound leaf. Shape: Linear, slightly broad based with outward extending apices. Margins: Finely serrated. Color: Yellow-Green Group 144A.

*Petiole*.—Length: About 31 mm. Diameter: 2 mm. Upper surface color: Yellow-Green Group 144A. Lower surface color: Yellow-Green Group 144A.

*Rachis*.—Length: About 75 mm. Upper surface color: Yellow-Green Group 147A. Lower surface color: Yellow-Green Group 147B.

*Leaflet*.—Quantity: Normally 7 leaflets. Margins: Serrated. Size: Terminal leaflets are about 83 mm long, 50 mm wide. Shape: Generally elliptical. Base: Rounded. Apex: Acute and mucronate. Texture: Smooth on the upper and lower surface. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botiytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren036' substantially as described and illustrated herein.

* * * * *